United States Patent [19]

Nischik et al.

[11] 4,013,522
[45] Mar. 22, 1977

[54] METHOD AND APPARATUS FOR MEASURING THE CONCENTRATION OF CARBON MONOXIDE

[75] Inventors: Herbert Nischik, Erlangen; Ferdinand von Sturm, Erlangen-Buchenbach, both of Germany

[73] Assignee: Siemens Aktiengesellschaft, Munich, Germany

[22] Filed: Jan. 20, 1975

[21] Appl. No.: 542,549

[30] Foreign Application Priority Data

Jan. 23, 1974 Germany .......................... 2403164
Nov. 15, 1974 Germany .......................... 2454285

[52] U.S. Cl. .......................... 204/1 T; 204/195 R
[51] Int. Cl.² .................. G01N 27/30; G01N 27/46
[58] Field of Search .......... 204/1 K, 195 R; 324/29
[56] References Cited

UNITED STATES PATENTS

| | | | |
|---|---|---|---|
| 3,403,081 | 9/1968 | Rohrback et al. | 204/1 T |
| 3,776,832 | 12/1973 | Oswin et al. | 204/1 K X |
| 3,852,169 | 12/1974 | Kring et al. | 204/1 K |
| 3,878,080 | 4/1975 | Luck | 204/195 P |
| 3,880,722 | 4/1975 | Beltzer | 204/1 K |
| 3,957,610 | 5/1976 | Falkenburg et al. | 204/195 R |

*Primary Examiner*—G. L. Kaplan
*Attorney, Agent, or Firm*—Kenyon & Kenyon Reilly Carr & Chapin

[57] ABSTRACT

A method for determining the concentration of carbon monoxide in the air along with a measuring electrode for carrying out the method in which the degree of inhibition of an electrochemical reaction caused by the carbon monoxide, in particular the inhibition of a cathodic oxygen reduction, is determined. Preferably the measurement is made with the electric potential held constant and the change in current taking place during inhibition used as a measure of concentration.

17 Claims, 9 Drawing Figures

METHOD AND APPARATUS FOR MEASURING THE CONCENTRATION OF CARBON MONOXIDE

BACKGROUND OF THE INVENTION

This invention relates to the determination of concentrations of carbon monoxide in general and more particularly to an improved method and apparatus for making such a determination.

There is a requirement for measuring the concentration of carbon monoxide in many different areas. For example carbon monoxide emissions from industrial plants, motor vehicles and domestic heating plants must be measured in many instances. With recent emphasis on occupational safety the need for measurement and recording of the carbon monoxide content of the air resulting from these types of emissions has been recognized.

For the purpose of measuring carbon monoxide in emissions from various sources and for measuring the carbon monoxide level in a particular area various measurement principles have been used. In particular methods utilizing a direct chemical reaction, methods including a combustion chamber and measurement of the conductivity of a reaction solution, methods using gas chromatography, methods using measurement of the heat change and methods using measurement of infrared absorption have been used (see VDI-Berichte No. 180: Carbon monoxide - generation, measurement and criteria of effects, VDI-Verlag GmbH, Duesseldorf, 1972, page 6 to 9). These known methods of measuring CO concentrations are not completely satisfactory. In particular they are not well suited for measurements in an area where personnel are exposed to concentrations of carbon monoxide. Furthermore in general they exhibit an appreciable sensitivity to other gases (cross sensitivity), so that interfering gases must be removed from the test sample prior to measurement. In addition the lowest detection limit in commercially available equipment which is suitable for automated anaylsis is about 10 ppm. (1 ppm corresponds to 0.0001% by volume).

However, in an area in which personnel are exposed to concentrations of carbon monoxide it is necessary that concentrations near and below 10 ppm be measured exactly. In many countries exposure levels have been established. For example in the Federal Republic of Germany the following Maximum Immission Concentration values were approved as early as 1967: 8 ppm of CO for 24 hours, 16 ppm of CO for 8 hours and 80 ppm of CO for 1 hour. In the U.S. even lower values have been established: 9 ppm of CO for 8 hours and 35 ppm of CO for 1 hour. By comparison the CO content of natural air, away from all civilization, is 0.012 ppm. Thus, the range of concentrations of carbon monoxide which must be measured extends far below 50 ppm which in Germany is the maximum permissible work station concentration.

In view of these recent requirements for maintaining low and safe levels of carbon monoxide in work areas the need for a method which is simple and can be automatically carried out and which can be used for measuring both emissions from polluting devices as well as measuring concentrations to which personnel are exposed is evident. Furthermore, such a device which exhibits little or no cross sensitivty and which permits determining low CO concentrations accurately, i.e., concentrations between 0 and 50 ppm is required.

SUMMARY OF THE INVENTION

The present invention provides such a method and a apparatus for carrying out that method. The present invention achieves this by determining the degree of inhibition of an electrochemical reaction caused by the carbon monoxide being measured. Herein, inhibition or inhibiting an electrochemical reaction referes to the effect of partial blocking of the electrocatalyst used in the reaction by the carbon monoxide resulting in a diminished electrode reaction.

In accordance with the present invention the CO measurement is preferably carried out such that the degree of inhibition of a cathodic oxygen reduction, caused by carbon monoxide is determined. This method, in which the CO contained in an oxygen containing gas is determined, is particularly useful for measuring the content of CO in air. However, it is also possible to determine CO concentration through the degree of inhibition of the anodic oxidation of an alcohol such as methanol, glycol or glycerin. When performing the method in this manner the alcohol is dissolved in the electrolytic liquid.

In the method of the present invention the electrode potential is preferably kept constant and the change of electric current which takes place during inhibition used as a measure of the CO concentration. This type of method in which the electric potential or voltage is held constant will be hereinafter referred to as the potentiostatic method of CO determination. It is possible, however, to measure the CO concentration using a constant current or galvanostatic method. In such a case the determination of CO concentration is accomplished by observing the change of electrode potential which takes place due to the CO inhibiting the reaction while the current is maintained constant.

In carrying out the method of the present invention it is preferred that the noble metal, particularly palladium be used as the electrocatalyst. Noble metal catalysts are particularly advantageous since the greatest inhibition effect takes place with these. If palladium is used as the electrode material measurements are generally carried out in the potential range of +150 to −650 mV and more particular in the range of −150 to −350 mV. The voltages are measured with respect to an $Hg/Hg_2SO_4$ electrode with 1 m $H_2SO_4$ as electrolytic liquid. By operating in this manner the greatest relative current changes are obtained as shown by potentiodynamic measurements. Other catalysts which may be used are for example platinum, cobalt phosphide $CoP_3$ and iron phosphide $FeP_2$. To preclude a reaction with $CO_2$ which might be present, an acid electrolytic liquid, preferably aqueous sulphuric acid is advantageously used in the method of the present invention. Other electrolytic liquids which can be considered for the method are phosphoric acid and in addition alkaline electrolytes. With the method of the present invention CO contents down to 0.01 ppm can be detected. Thus, the method of the present invention is particularly well suited for determining CO concentrations in the range of 0 to 50 ppms which are required for making measurements of areas where personnel are exposed to CO. Furthermore, the method exhibits little cross sensitivity. When using palladium for instance, $CO_2$ and gasoline vapor, i.e., hydrocarbons, show no interference effects. The gases $H_2$ and $Cl_2$ along with $NH_3$, $SO_2$ and $H_2S$ interfere only if they are present in high concentrations. Should such be the case these gases are then separated prior to the CO determination.

DETAILED DESCRIPTION OF THE PREFERRED EMBODIMENT

Electrode materials and the electrode reactions of the present invention can employ gas tight supported electrodes with gas permeated electrodes or with smooth electrodes. If electrode material in powdered form is employed it can advantageously be used in the form of what are referred to as supported electrodes (see F. v. Sturm, "Elektrochemische Stromerzeugung" (Electrochemical generation of current), vol. 5 of the Series "Chemische Taschenbuecher", Verlag Chemie GmbH, Weinheim/Bergstrasse, 1969, page 109). These electrodes are double layered electrodes with a working layer containing the electrocatalyst, i.e. the electrode material, with a fine-pore inactive cover layer which is adjacent to the electrolytic liquid. This cover layer is gastight in an electrolyte saturated condition. With such an electrode, the gas to be examined is fed to the working layer. Examinations are performed in half cells which have a design in which the working electrode is arranged in a plastic housing such as a housing of Plexiglass. A pressure plunger is used to press the working layer on the cover layer which is supported against the electrolyte chamber by a fine mesh screen and perforated sheet. The geometric electrode surface is appoximately 12.5 cm$^2$. When using 1 m $H_2SO_4$ as the electrolytic liquid, the cover layer consists of an asbestos paper containing a cation exchanger and a hydrophilic binder (see German Offenlegunsschrift 2,104,333) about 0.4 mm thick. The fine mesh screen consists of polypropylene fabric and the perforated sheet, which is about 1 mm thick, of tantalum. Contact of the working layer is established by means of a carbon fabric and a gold wire. An $Hg/Hg_2SO_4$ electrode in 1 m $H_2SO_4$ as an electrolyte liquid is used as a reference electrode. A similar arrangement will be described in detail below in connection with FIG. 4. The measurements are carried out at room temperature (about 23° C) and a gas pressure of about 14 N/cm$^2$. To avoid concentration variations, it is advantageous to work with a high rate of gas flushing at the working electrode (flow rate about 20Nl/h).

Figure 1:
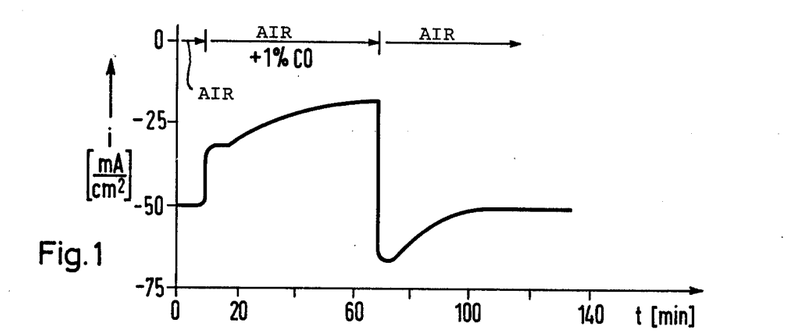
FIGS. 1 and 2 are curves illustrating measurement results using two different electrodes in the potentiostatic mode of operation.
Figure 2:
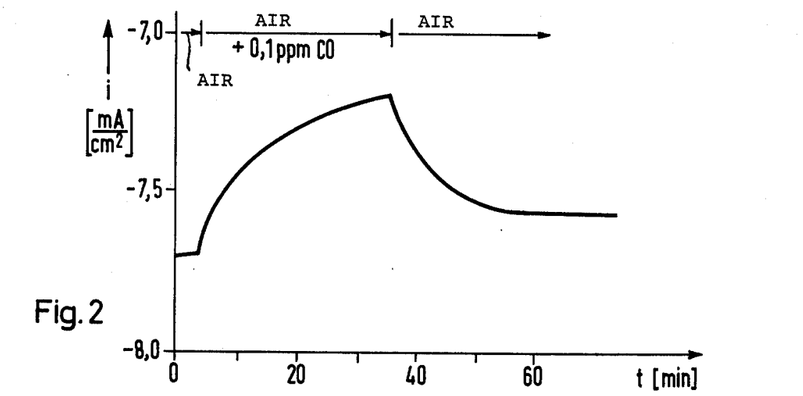
Figure 3:
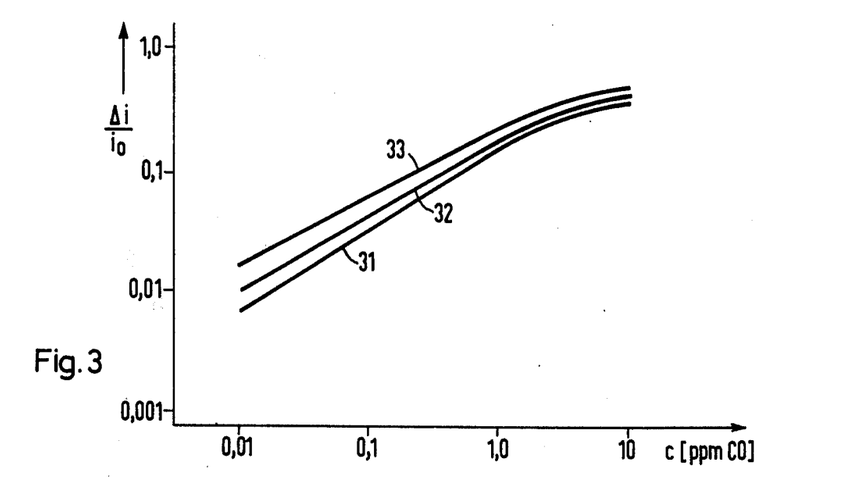
FIG. 3 illustrates calabration curves for the determination of the CO content in air.

The results obtained in such an arrangement and using the method of the present invention are illustrated in FIGS. 1, 2 and 3. In determining the inhibition of the cathodic oxygen reduction, the gas mixtures fed to the working electrode were not prepared from atmospheric air since its CO content varies and generally is not known. Instead, commercially available synthetic air with 80% by volumne of $N_2$ and 20% by volume of $O_2$ was used. Be carefully adding carbon monoxide, gas mixtures with a predetermined CO content were made from this synthetic air. Snythetic air without the addition of CO was used as a reference gas. While operating in a potentiostatic mode, at the start of the test the working electrode was loaded potentiostatically to the potential at which the subsequent measurements were to be performed while CO free air was supplied. This was continued until the cathodic current caused by the reduction of the oxygen in the air had reached a value as constant as possible. When $CO_2$ containing air was added, a reduction of the current was always observed. When going back to CO-free air the inhibition was cancelled and after a period of time the current again reached the initial value, i.e., the poisoning of the catalyst by the CO was reversed.

FIG. 1 shows the results obtained with an electrode of platinum black, coating thickness 10 mg/cm$^2$ with a potentiostatic loading at −640 mV (referred to $Hg/Hg_2SO_4$). With a CO-free air fed in, a constant cathodic current of about 50 mA/cm$^2$ is reached after a short time. After switching to air with a content of approximately 1% by volumne of CO, the current density drops rapidly to about 30 mA/cm$^2$ and then, within about an hour, further to 20 mA/cm$^2$. After switching again to CO-free air, the cathodic current density first reached a maximum of about 70 mA/cm$^2$ before adjusting itself to the initial value of about 50 mA/cm$^2$ again.

As will be described in more detail below, it has been discovered that it is not necessary to wait for equilibrium at the electrode. In other words, with the example given above it is not necessary to wait until the cathodic current has decreased to 20 mA/cm$^2$. Instead the CO concentration can be determined within a short time, e.g., within about 1 minute.

Corresponding results are obtained using a palladium sponge as the electrode material. Palladium has an advantage over platinum in that the values adjust themselves faster and the current changes are, in addition, relatively large. That is to say greater sensitivity is obtained even at lower CO concentrations. With a coating thickness of about 10 mg/cm$^2$ at a potential of about −150 mV a current density of about 25 mA/cm$^2$ which drops to a value of about 2 mA/cm$^2$ immediately after switching to a gas containing CO is obtained. When going back to CO-free gas, the initial value adjusts itself again quickly.

A further increase of the sensitivity can be achieved by using a gas-flow electrode instead of a supported electrode. In such porous electrodes the gastight cover layer of the supported electrodes is replaced by a porous layer. In the present method this is generally a carbon fabric. The gas is then conducted through this porous electrode and enters the adjoining electrolytic liquid. FIG. 2 illustrates the curve obtained using a potential of −340 mV with a gas flow electrode containing 10 mg of palladium sponge per cm$^2$. It is evident from the Figure that even with a content of 0.1 ppm of CO in the synthetic air a distinct reduction in the current is observed.

Further investigations have shown that CO concentrations down to 0.01 ppm can be detected. From a large number of measurement results, calibration curves were prepared and are illustrated on FIG. 3. These curves represent the dependence of the relative current density changes $\Delta i/i_0$ ($i_0$=current density for operation in CO-free air, $\Delta i$=difference of the current density for operation with CO-free air and air containing CO) on the CO concentration c in the air. The curves 31, 32 and 33 are for a gas flow electrode with 10 mg of palladium sponge per $cm_2$, 1 m $H_2SO_4$ used as the electrolytic liquid, an ambient temperature of 23° C, and a potential of −340 mV referred to an $Hg/Hg_2SO_4$ electrode. Curve 31 is for a measuring time of 250 seconds. That is it is used if the measured value is observed 250 seconds after switching from the CO-free air to CO containing air. Curve 32 is for a measuring time of 500 seconds and curve 33 for a measuring time of 2000 seconds. From these calibration curves it becomes clear that the carbon monoxide concentration can be accurately determined down to concentrations of 0.01 ppm within a very short time i.e., after approximately 4 minutes as shown by curve 31. It is thus not necessary to wait for the equilibrium of the carbon monoxide to adjust itself at the electrode.

To operate in the galvanostatic mode of operation, (constant current) the following procedure can be followed. A smooth electrode in the form of a palladium sheet with an area of 2 $cm^2$ is immersed in a 1 m $H_2SO_4$ electrolytic liquid at 23° C. A quantity of about 500 ml of electrolytic liquid is sufficient. Before the start of the test the electrode is loaded for about 3 hours galvanostatically with about −100 $\mu A/cm^2$. During the measurement itself the palladium electrode is loaded, also cathodically, with 100 $\mu A/cm^2$ while CO-free synthetic air is supplied. At this time a potential of about −50 mV results when measured against an $Hg/Hg_2SO_4$ electrode. If air with a content of 100 ppm of CO is then fed to the electrode, the potential drops to about −130 mV. The air or the air/CO mixture is thereby fed into the electrolytic liquid in a quantity of about 3 l/hr. while the electrolytic liquid is stirred.

As noted above, the CO concentration can also be determined by measuring the degree of inhibition of the anodic oxidation of alcohols. A potentiostatic determination under the following conditions has been found advantageous:

Electrochemical oxidation of methanol:
Electrolyte: 1 m $CH_3$ OH in 1 m $H_2SO_4$;
Electrode: Supported electrode with a Pd/Pt alloy with 20% by weight of Pt as the electrocatalyst (coating thickness: about 10 $mg/cm^2$);
Potential: +0.5 V (with respect to a standard hydrogen electrode)
Electrochemical oxidation of glycerin:
Electrolyte: 1 m glycerin in 1 m $H_2SO_4$;
Electrode: Platinum-plated platinum;
Potential: +0.7 V (with respect to the standard hydrogen electrode)
Electrochemical oxidation of ethylene glycol:
Electrolyte: 1 m ethylene glycol in 1 m $H_2SO_4$;
Electrode: Platinum-plated platinum
Potential: +0.6V (with respect to the standard hydrogen electrode).

The efficiency of the method of the present invention can be further improved by alternating the anodic and cathodic polarization after the electrode has been used for a certain operating time. With anodic loading it is advantageous to proceed until oxygen is developed and with cathodic loading until hydrogen is developed. In this manner the electrode surface is cleaned and a defined potential always adjusts itself. The polarization can be carried out by briefly polarizing anodically and cathodically in alternating order. However, the loading can also be accomplished potentiodynamically. If, for example a Pd electrode is used, it is accomplished by alternating polarization between a loading as during operation at a value of −340 mV and a loading thereafter at a value of +350 mV so that the carbon monoxide which is still present is oxidized to carbon dioxide within a few seconds and is removed. As a result the full catalytic activity of the electrode is restored within a very short time. Because of the short time duration, this alternating reverse polarization can be performed after each measurement. Alternatively it can be carried out at regular intervals, e.g., at spacings of 1 hour.

The method for determining concentration of carbon monoxide which has been described above can be further substantially improved by feeding to the electrode, in an alternating manner, gas containing carbon monoxide and a reference gas prepared from the gas containing the carbon monoxide with the carbon monoxide removed.

In principle, the CO content of the air can be calculated from stationary values, i.e., the electrode can be operated in the potentiostatic mode with the gas containing carbon monoxide i.e., the measuring gas, being supplied thereto continually and the current being a measure of CO concentration which is obtained with a calibration curve. Because the current depends heavily on such operating conditions as flow velocity of the measuring gas, pressure, temperature, composition of the electrolyte and the electrode potential, which must be kept constant, generally only CO concentrations above 10 ppm can be determined rapidly and reliably. Furthermore it is advisable to check the zero point more frequently, using CO-free air. For measuring lower CO concentration the dynamic mode of operation is far better suited. In this method, also referred to as the pulse method, the electrode is first operated potentiostatically with CO-free reference gas until a constant current $i_0$ flows. This current is caused by the cathodic reduction of the oxygen in the air. After a constant current has adjusted itself, a pulse of the measuring gas is briefly applied to the electrode, i.e., it is operated with the measuring gas for a short time. The current change $\Delta i$ is determined at the end of the pulse. The quotient $\Delta i/i_0$ in this method is a measure of the CO content of the air. The length of the pulse along with the subsequent recovery phase depends on the kind of catalyst used, the desired sensitivity and the desired sequence of measuring points. Important advantage of the pulse method results from the fact that even low CO concentrations in air can be determined accurately and quickly. By checking the zero point prior to each measurement, the sensitivity of the measuring method is also considerably increased.

The fact that the reference gas used is prepared from the measuring gas also contributes significantly to the increased measuring sensitivity. This is a direct result of the fact that both the CO-free reference gas and the measuring gas have the same oxygen concentration. In principle, the CO-free reference gas could be taken from a compressed gas bottle. However, making compressed gas bottles available, replacing them carefully, and the space required thereby would result in considerable disadvantages.

To prepare a CO-free reference gas from the measuring gas to be examined, activated carbon filters can be used to absorb the CO from the measuring gas. However by using this procedure the used up filters must be regularly replaced. To avoid such problems it is preferable that the carbon monoxide be removed from the gas containing it using catalytic oxidation of the carbon monoxide to carbon dioxide. If such is done the CO determination can be simply automated and requires only a minimum of maintenance.

To carry out such a catalytic oxidation of carbon monoxide to carbon dioxide, Hopkalit, which consists of a mixture of metal oxides can be used as the catalyst. However, since the lifetime of this catalyst is limited by the moisture of the air, platinum asbestos is preferably used for this catalytic oxidation of the carbon monoxide.

As noted above, it is an important advantage of preparing the CO-free reference gas directly from the measuring gas that in this manner the same oxygen content is found in both the measuring and reference gas. This is particularly important at low CO concentration since the change in the oxygen content would cause a change in the current and could therefore falsify the measurement result.

For carrying out the method of the present invention, a measuring electrode having a design as follows is particularly advantageous. In an electrode body, which consists preferably of plastic, a recess is provided in which are arranged in sequence, starting at the bottom, a pressure plunger, at least one screen for making contact and distributing the gas, a catalytically active layer, a cover layer, at least one support frame and a pressure ring. In the area above the pressure plunger, i.e., in the area on the side of the pressure plunger facing away from the catalytically active layer, the electrode body is provided with a hole for receiving a clamping screw. The electrode body will include, in addition, two further holes for the supply and removal of gas to the catalytically active layer. Furthermore, means are provided to connect the catalytically active layer in an electrically conducting manner to an external contact.

Figure 4:
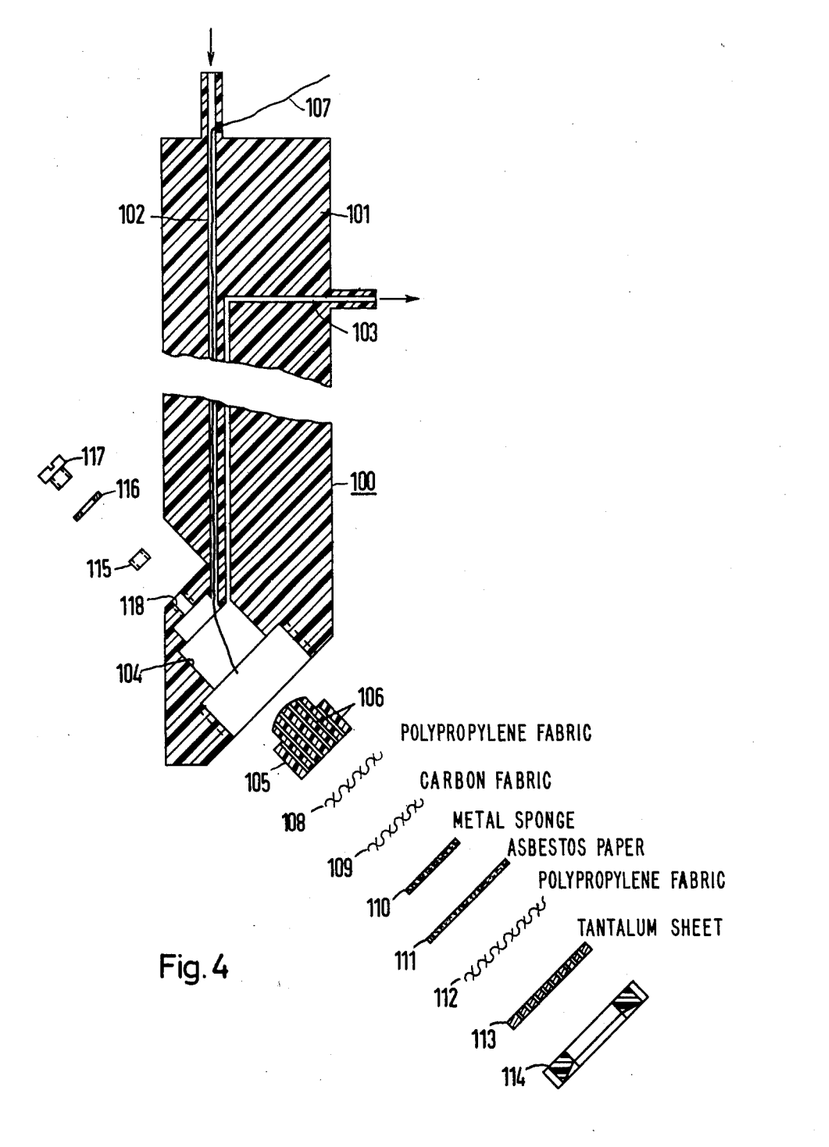
FIG. 4 is an exploded view of a measuring electrode according to the present invention.

An electrode of this nature is illustrated on FIG. 4 with a scale of 2:1. The electrode designated generally as 100 is what is referred to as a supported electrode and is adapted to the special requirements of the present invention. The measuring electrode 100 includes a rod-shaped electrode body 101 made of polymethacrylic acid ester such as that sold under the trademark of Plexiglass, with a diameter of 18 mm. The electrode body 101 includes two holes 102 and 103 for feeding and discharging the measuring gas. In its lower portion the electrode body is doubled and contains a recess 104 which is known as the electrode chamber. A pressure plunger 105 of Plexiglas is first inserted therein. The pressure plunger 105 is provided with longitudinal holes 106 to allow access for the measuring gas from the canal or hole 102 to the electrode itself. The holes therein also permit measuring gas being discharged through the channel 103. Through one of the holes or channels 106 and through the channel 102, a gold wire 107 is led and establishes contact between the catalytically active working layer 110 of the electrode and an external contact through a gold plated polypropylene fabric 108 which is used for distributing the gas and making contact and a fine carbon fabric 109 serving as a support and for making contact. The working layer 110 will consist, for example, of a platinum or palladium sponge. The components from the pressure plunger 105 through the working layer of the electrode have a diameter of 8 mm. Following the working layer there is provided an asbestos paper cover layer 111, a polypropylene fabric 112 for support purposes along with a perforated tatalum sheet 113. These all have a diameter of 12 mm. The 2 mm wide rim of the asbestos paper cover layer 111 which protrudes beyond the working layer 110 is used as a seal. These latter individual parts are held together and the asbestos paper cover layer 111 sealed by means of a pressure ring 114 of Plexiglas inserted behind the perforated tantalum sheet 113. The pressure ring 114 is screwed into the recess 104 of the electrode body 101 and tightened. To press on and seal the arrangement from the opposite side, a clamping screw 115 of tantalum, a gasket 116 of fluorine elastomer such as that sold under the trademark Viton, and a sealing screw 117 of Plexiglas are arranged in a hole 118 in the electrode body 101 which opens into the recess 104.

Figure 5:
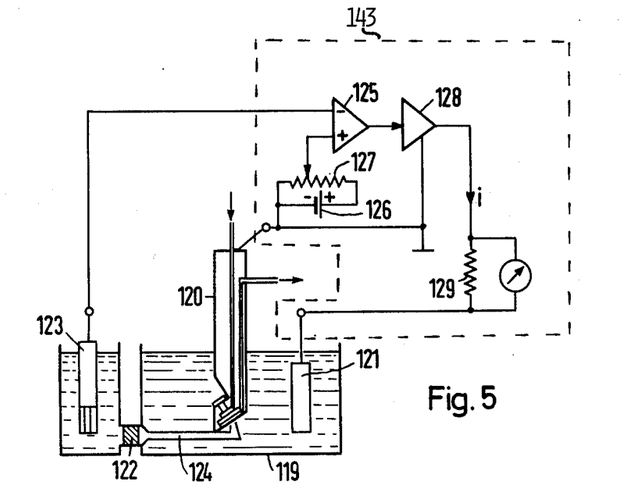
FIG. 5 is a block diagram illustrating an arrangement for determining CO concentrations using the potentiostatic method.

For practicing the method of the present invention, an electrode such as that of FIG. 4 along with a counterelectrode and reference electrode are built into a measuring cell such as that shown on FIG. 5. This Figure illustrates the arrangement for carrying out a potentiostatic mode of operation for CO determination. Shown in FIG. 5 is a measuring electrode 120 such as that of FIG. 4 along with a platinum sheet 121 used as a counter electrode disposed in a tank 119 having a portion on the right hand side filled with an electrolytic solution of 1 m $H_2SO_4$. The left hand side of the tank, separated therefrom by a porous ceramic ion-permeable diaphragm 122, is filled with a saturated $K_2SO_4$ solution and has disposed therein a reference electrode 123 which is an $Hg/Hg_2SO_4$ electrode. A Luggin probe 124 extends from the diaphragm 122 to the measuring electrode 120. The electrodes are connected to a potentiostat, i.e., a constant potential source which includes an auxiliary voltage source, a potentiometer, an operational amplifier, an output amplifier and a measuring resistor. The operational amplifier 125 is used as a differential amplifier. The reference electrode 123 is connected to its inverting input. Its non-inverting input is connected to the auxiliary voltage source which comprises a battery or the like 126 and a potentiometer 127. Thus there will be applied to the inverting input of the amplifier 125 the measured voltage between the measuring electrode 120 and the electrode 123 which constitutes an actual value. To the noninverting input a reference voltage obtained from the potentiometer 127 will be provided. The measured voltage at the inverting input corresponding to the potential difference between the measuring electrode and the reference electrode has a very high impedance and thus carries essentially no current. Whenever a small deviation of the actual value from the reference value occurs, the voltage differences immediately amplified by the operational amplifier 125 and provided as a control variable through an output amplifier 128. In response thereto the output amplifier 128 immediately changes the current $i$ between the measuring electrode 120 and the counterelectrode 121 such that the potential of the measuring electrode 120 with respect to the reference electrode 123 corresponds to the set reference value and the voltage difference at the input of the operational amplifier 125 is zero. A measuring resistor 129 is provided to detect the current $i$ in the form of a voltage proportional thereto.

The current $i$ in the measuring cell 119 flowing between the counterelectrode 121 and the measuring electrode 120 is thus controlled by the potentiostat such that the potential of the current carrying measuring electrode 120 relative to the currentless reference electrode 123 corresponds to a predetermined reference voltage and is kept constant at its instantaneous value regardless of the electrochemical processes taking place. By detecting the current $i$ flowing it is then possible to ascertain the type of electrochemical activity occurring at the measuring electrode 120. As explained above a reduction of the current from $i_0$ to $i_1$ at the output of the output amplifier 128 is an indication that a partial poisoning of the measuring electrode with CO has taken place, i.e., the cathodic oxygen reduction has been inhibited. Typical measuring conditions for measuring cell are as follows: a catalytically active working layer in the form of a palladium sponge with a coating of 10 mg/cm$^2$ is used with an electrolytic liquid of 1 m H$_2$SO$_4$ at a temperature of 23° C. The reference electrode is an Hg/Hg$_2$SO$_4$ electrode disposed in a saturated K$_2$SO$_4$ solution. The counterelectrode is a platinum sheet 1 cm$^2$. The gas pressure of the measuring gas is 0.4 bar (4 N/cm$^2$) above ambient pressure and is supplied with a flow velocity of 10 Nl/hr. The potential of the measuring electrode referred to the reference electrode is −340 mV.

Figure 6:
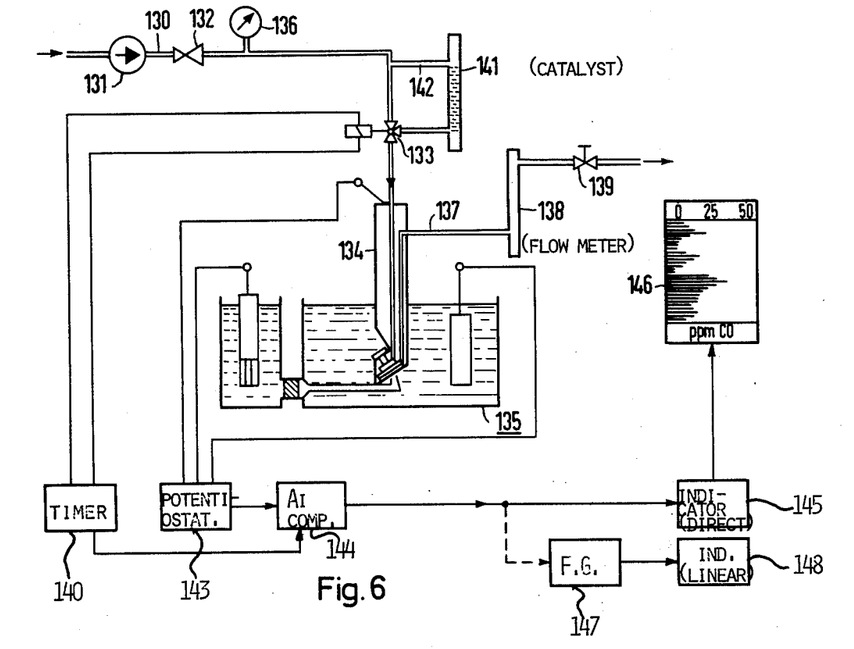
FIG. 6 is a block diagram illustrating a complete measuring facility for making CO measurements according to the present invention.

FIG. 6 illustrates a complete setup of a measuring facility for determining CO using the method of the present invention along with the apparatus as shown on FIGS. 4 and 5. The measuring gas is fed to the electrode 134, corresponding to electrode 120 of FIG. 5, in the cell 135 through a pump 131, a pressure reducer 132 and a magnetic valve 133. A manometer 136 is also provided in the inlet line 130. The measuring gas leaves the measuring cell 135 through the line 137 in which a flow meter 138 is arranged with the flow velocity of the measuring gas adjusted by means of a fine control valve 139 at the end of the line 137.

The magnetic valve 133 which is arranged ahead of the measuring cell 135 is a three way valve. Its position is controlled by a timer 140. This valve has the capability of connecting the line 130 directly with the measuring cell 135. In such a case the measuring gas will contain carbon monoxide, i.e., the pump 131 may be pumping the ambient air in a work space where the exposure to carbon monoxide can be determined. The three way valve can also connect the input to the measuring electrode 134 with a catalyst 141. In that case the measuring gas will flow through the line 130 through the line 142 and the catalyst 141 before reaching the measuring electrode 134. The catalyst will be of a type which will remove or convert the CO in the measuring gas so that a measuring gas free of CO will be provided to the measuring cell 135. Typically the bed of catalyst 141 can contain 2 g of platinum asbestos. During a life test a catalyst of this nature has shown its initial activity even after 2000 hours of operation. In accordance with the method described above, the timer 140 will be set to first admit carbon monoxide free air to the measuring cell 135 and then admit measuring gas with carbon monoxide. This process can be alternately carried out to obtain a series of measurements over a prolonged time period. The alternation between the reference gas and the measuring gas will produce at the potentiostat 143 a current change from $i_0$ to $i_1$ in the above described manner. Potentiostat 143 which will be as shown on FIG. 5. The output from its measuring resistor 129 coupled to a $\Delta i$ computer 144. The $\Delta i$ computer 144 will include conventional sample and hold circuits for sampling and holding the values $i_0$ and $i_1$. Sample commands will be provided in conventional fashion from the timer 140. The sample and hold circuits for sampling and holding the values $i_0$ and $i_1$ are coupled to a summing arrangement such as an operational amplifier to determine the current change $\Delta i = i_0 - i_1$. Also included is an analog divider for forming the quotient $\Delta i/i_0$, i.e., it has as inputs the outputs of the differential amplifier determining $\Delta i$ along with the output of the sample and hold circuit containing the value $i_0$. The quotient $\Delta i/i_0$ is a measure of the CO content in the air. It can be provided directly to a direct reading indicator 145 which is then coupled to a chart recorder 146. Alternatively, it can be coupled through a function generator 147 which has a transfer function corresponding to the calibration curve of the apparatus with the output of the function generator provided to a linear indicator 148.

Figure 7:
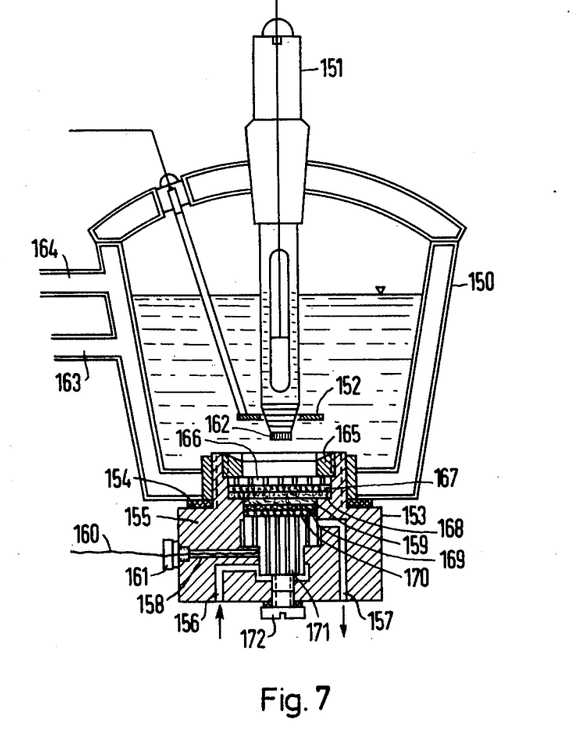
FIG. 7 illustrates an alternate embodiment of a measuring cell according to the present invention.

FIG. 7 illustrates a further embodiment of a measuring cell according to the present invention. The measuring cell includes a vessel 150 filled with 1 m H$_2$SO$_4$ electrolyte in which is disposed a reference electrode 151 of the type Hg/Hg$_2$SO$_4$ contained in a saturated K$_2$SO$_4$ solution. Also disposed in the electrolyte is a ring shaped sheet of platinum 152 providing the counter electrode. The measuring electrode 153 is arranged in the bottom of the vessel 150 and is sealed with a gasket 154 made of a fluorine elastomer such as Viton. The design of the measuring electrode 153 is essentially the same as the measuring electrode 100 of FIG. 4. However, in contrast to the embodiment of FIG. 4 the electrode body 155 of the measuring electrode 153 is not bevelled and in addition to containing holes 156 and 157 for feeding and discharging gas it includes a further hole 158 through which a wire 160 is passed to make the electrical connection between the catalytically active working layer 159 and external contact. Hole 158 is closed by a seal 161. The measuring electrode 153 is arranged directly next to the reference electrode 151, i.e., at the diaphragm 162, so that a Luggin probe is not required in this embodiment. In addition, the vessel 150 is a double layer vessel and has connections 163 and 164 through which a fluid may be provided to maintain the temperature at a predetermined level. This measuring cell has a very compact design. In addition, because of the upright arrangement of the measuring electrode in the bottom of the vessel 150 gas bubbles can not collect in the region of the pressure ring 165 and the perforated sheet 166. If gas bubbles were to collect such would falsify the measurement result. The individual components of the measuring electrode, i.e., electrode body 155, the pressure ring 165, the perforated sheet 166, the screen 167, the cover layer 168, the working layer 159, the screens 169 and 170 along with the pressure plunger 171 and seal 172 correspond to those of the embodiment of FIG. 4.

Figure 8:
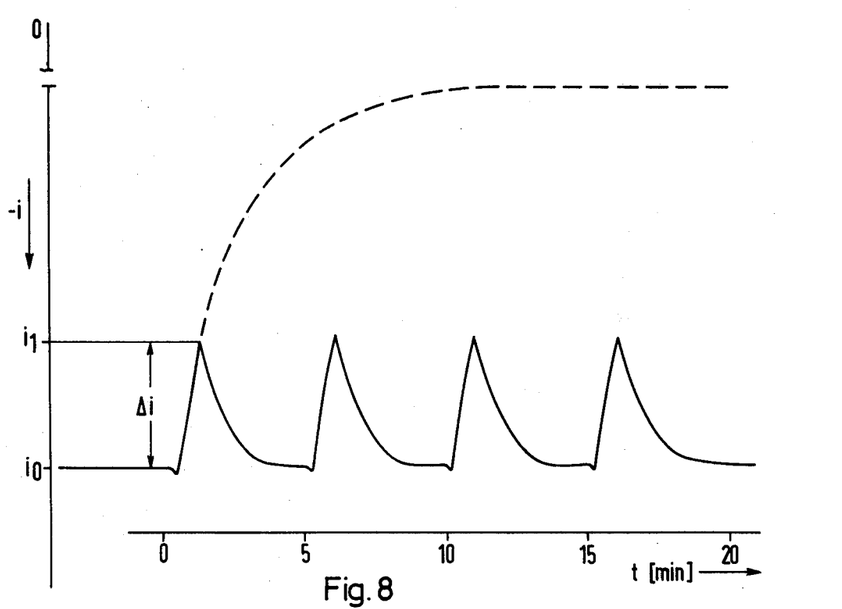
FIGS. 8 and 9 are curves illustrating the response obtained when carrying out a pulsed operation according to the method of the present invention.

FIG. 8 is a curve which futher illustrates the principle of CO determination using pulsed operation. On the figure is a current wave form. For the example shown the measuring cell is first operated with reference gas. During this time a constant current $i_0$ adjusts itself. With reference to FIG. 6 this represents the condition where the timer 140 has positioned three way valve 133 such that the measuring gas is led through the catalyst 141. Subsequently, unmodified measuring gas with a CO content of 5 ppm is conducted through the measuring cell for about 5 seconds, the timer 140 now switching the three way magnetic valve 133 so that the measuring gas is provided directly to the measuring cell. As shown on FIG. 8 this manifests itself in a pronounced peak in the current wave form, i.e., the current goes from $i_0$ to $i_1$ which is reached, depends on the width of the pulse i.e, the amount of time during which the gas or CO is permitted to flow through the cell. Through this figure it becomes evident that a state of equilibrium would be reached in the cell only after the gas with the CO had flowed through the cell for about 15 minutes. Recovery back to the value $i_0$ would take another 30 minutes. Thus, if such were done, measurements could be taken only every 45 minutes. However, by operating in a pulsed mode, measurements can be taken much more often. As illustrated by FIG. 8, after approximately 5 minutes the system is again ready to take another measurement. Once again the illustrated condition is one where the pulse duration of the measuring gas containing CO is approximately 5 seconds after which the cell is operated for approximately 5 minutes with the reference gas not containing CO. The necessary pulse duration will of course depend on the required sensitivity. For example if CO contents below 1 ppm are to be accurately measured it is advisable that the pulse duration be about 10 to 60 seconds and the measurement point interval about 10 to 30 minutes.

Figure 9:
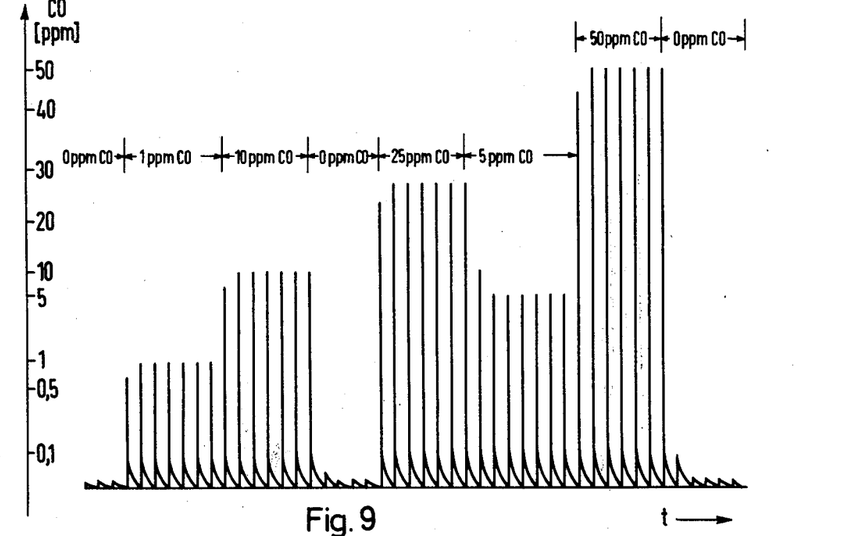

FIG. 9 is a further current waveform. This is typical of the pattern one would expect to get from a chart recorder such as the recorder 146 of FIG. 6. In the example shown operation was carried out with calibration gases of different CO concentrations. Note that the recorded value here is the quotient $\Delta i/i_0$. By means of measurements such as these with different CO concentrations calibration curves can be prepared with the CO content a function of the quotient $\Delta i/i_0$.

Thus an improved method and apparatus for making CO determinations has been shown. Although specific embodiments have been illustrated and described, it would be obvious to those skilled in the art that various modifications may be made without departing from the spirit of the invention which is intended to be limited solely by the appended claims.

What is claimed is:
1. A method for determining the concentration of carbon monoxide in a measuring gas comprising the steps of:
   a. establishing an electrochemical reaction of the type causing current to flow using a electrolyte and a pair of electrodes, at least one of said electrodes being of a material whose activity is inhibited by carbon monoxide;
   b. feeding the measuring gas directly to said one of said electrodes; and
   c. determining the degree of inhibition of said electrochemical reaction which is caused by the carbon monoxide in said measuring gas.
2. The method according to claim 1 wherein said measuring gas is introduced into the electrolytic liquid which is in contact with one electrode.
3. A method of determining the carbon monoxide content in a measuring gas comprising the steps of:
   a. providing a porous electrode having a cover layer on the electrode side which in an electrolyte saturated condition is gas tight, said electrode including means for feeding a gas to and discharging a gas from it and for coupling with an external contact;
   b. providing a separate counter electrode;
   c. disposing said first and second electrodes in an aqueous sulphuric acid electrolyte;
   d. applying a potential to said porous electrode to establish a cathodic oxygen reduction;
   e. maintaining one of the potential and current of said electrodes constant;
   f. feeding the measuring gas containing carbon monoxide to said porous electrode; and
   g. measuring the change in the one of potential and current which is not held constant as a measure of the inhibition of said cathodic oxygen reduction by said carbon monoxide.
4. A method for determining the concentration of carbon monoxide in a measuring gas comprising the steps of:
   a. preparing a reference gas from the measuring gas by removing the carbon monoxide therefrom by catalytically oxidizing it to carbon dioxide through the use of a platinum asbestos catalyst;
   b. establishing an electrochemical reaction of the type causing current to flow using an electrolyte and a pair of electrodes;
   c. alternately feeding the measuring gas and the reference gas to one of said electrodes; and
   d. determining the degree of inhibition of said electrochemical reaction which is caused by the carbon monoxide in said measuring gas.
5. The method according to claim 4 wherein said electrochemical reaction is a cathodic oxygen reduction.
6. The method according to claim 5 wherein said electrochemical reaction is carried out with a constant electrode potential and wherein the change of electric current occurring due to the inhibition caused by said carbon monoxide is determined as a measure of the carbon monoxide concentration.
7. The method according to claim 5 wherein said electrochemical reaction is carried out with a constant current and the change in electrode potential which occurs due to inhibition by the carbon monoxide is used as a measure of the carbon monoxide concentration.
8. The method according to claim 4 wherein the electrode to which said measuring gas is provided is a noble metal electrode.
9. The method according to claim 8 wherein said electrode comprises palladium.
10. The method according to claim 4 wherein an electrolytic liquid which is an acid is used.
11. The method according to claim 10 wherein said acid is aqueous sulphuric acid.
12. The method according to claim 4 wherein the electrode to which said measuring gas is fed is a porous electrode having a cover layer comprising asbestos paper containing a cation exchanger and a hydrophillic binder on its electrolyte side which in the electrolyte saturated condition is gas tight.
13. The method according to claim 4 wherein the electrode to which the carbon monoxide containing gas is fed is a porous electrode wherein the carbon monoxide containing gas is conducted through the electrode into the electrolytic liquid.
14. The method according to claim 4 and further including the step of alternatingly subjecting the electrode to which said measuring gas is fed to reverse anodic-cathodic polarization to maintain catalytic activity.

15. A method for determining the concentration of carbon monoxide in a measuring gas comprising the steps of:
   a. establishing an electrochemical reaction of the type causing current to flow using an electrolyte consisting of aqueous sulphuric acid and a pair of electrodes;
   b. feeding the measuring gas to one of said electrodes; and
   c. determining the degree of inhibition of said electrochemical reaction which is caused by the carbon monoxide in said measuring gas.

16. A method for determining the concentration of carbon monoxide in a measuring gas comprising the steps of:
   a. establishing an electrochemical reaction of the type causing current to flow using an electrolyte and a pair of electrodes;
   b. feeding the measuring gas to one of said electrodes;
   c. determining the degree of inhibition of said electrochemical reaction which is caused by the carbon monoxide in said measuring gas; and
   d. alternatingly subjecting the electrode to which said measuring gas is fed to reverse anodic-cathodic polarization to maintain catalytic activity.

17. A measuring electrode for use in measuring carbon monoxide concentrations in a measuring gas comprising:
   a. an electrode body having a recess therein;
   b. a pressure plunger in the bottom of said recess;
   c. at least one contact making and gas distribution screen next to said plunger;
   d. a catalytically active layer for effecting an electrochemical reaction of the type causing a current to flow next to said screen;
   e. a cover layer next to said catalytically active layer;
   f. at least one support frame and a pressure ring next to said cover layer;
   g. means in said electrode body for applying pressure to said pressure plunger;
   h. said electrode body having holes therein for feeding and discharging gas to said catalytically active layer; and
   i. means for electrically connecting said catalytically active layer with an external contact.

* * * * *